(12) United States Patent
In et al.

(10) Patent No.: US 10,245,211 B2
(45) Date of Patent: Apr. 2, 2019

(54) POROUS ACUPUNCTURE NEEDLE AND METHOD FOR MANUFACTURING SAME

(71) Applicant: DAEGU GYEONGBUK INSTITUTE OF SCIENCE AND TECHNOLOGY, Daegu (KR)

(72) Inventors: Su Il In, Daegu (KR); Hye Rim Kim, Daegu (KR); Abdul Razzq, Daegu (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 92 days.

(21) Appl. No.: 15/120,633

(22) PCT Filed: Jul. 17, 2014

(86) PCT No.: PCT/KR2014/006505
§ 371 (c)(1),
(2) Date: Aug. 22, 2016

(87) PCT Pub. No.: WO2015/129967
PCT Pub. Date: Sep. 3, 2015

(65) Prior Publication Data
US 2017/0007499 A1   Jan. 12, 2017

(30) Foreign Application Priority Data
Feb. 26, 2014   (KR) .................. 10-2014-0022655

(51) Int. Cl.
| | | |
|---|---|---|
| *A61H 39/08* | (2006.01) |
| *A61M 5/158* | (2006.01) |
| *C25D 11/00* | (2006.01) |
| *C25D 11/34* | (2006.01) |

(52) U.S. Cl.
CPC ........... *A61H 39/086* (2013.01); *A61M 5/158* (2013.01); *C25D 11/005* (2013.01); *C25D 11/34* (2013.01); *A61H 2201/105* (2013.01); *A61M 2207/00* (2013.01)

(58) Field of Classification Search
CPC ..... A61H 39/086; C25D 11/005; C25D 11/34
See application file for complete search history.

(56) References Cited

U.S. PATENT DOCUMENTS

2011/0245856 A1 * 10/2011 Su ..................... A61H 39/086
606/189
2015/0027598 A1 * 1/2015 Seng .................... A61L 31/022
148/578

FOREIGN PATENT DOCUMENTS

| | | |
|---|---|---|
| JP | 2008079919 A | 4/2008 |
| KR | 1020080112759 | 12/2008 |
| KR | 1020110113589 | 10/2011 |

OTHER PUBLICATIONS

International Search Report and Written Opinion for PCT/KR2014/006505, dated Sep. 26, 2014.

* cited by examiner

*Primary Examiner* — Nathan R Price
*Assistant Examiner* — Tasnim Mehjabin Ahmed
(74) *Attorney, Agent, or Firm* — Norton Rose Fulbright US LLP

(57) ABSTRACT

The present invention relates to a porous acupuncture needle and a method for manufacturing the same and, more specifically, to a porous acupuncture needle, which has micro-sized or nano-sized holes formed on the surface thereof to maximize the specific surface thereof, and a method for manufacturing the same.

7 Claims, 6 Drawing Sheets

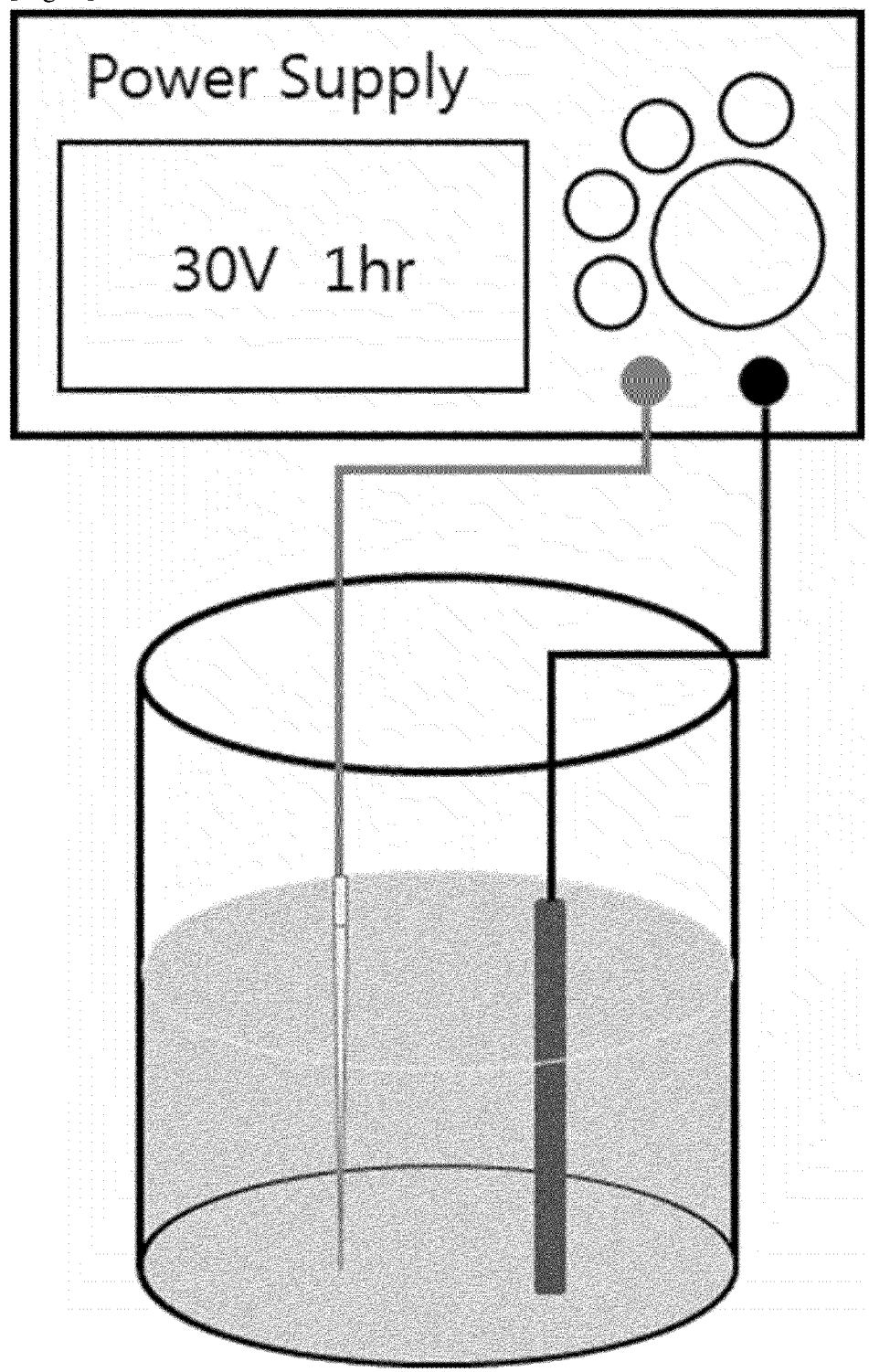
[Fig. 1]

[Fig. 2]
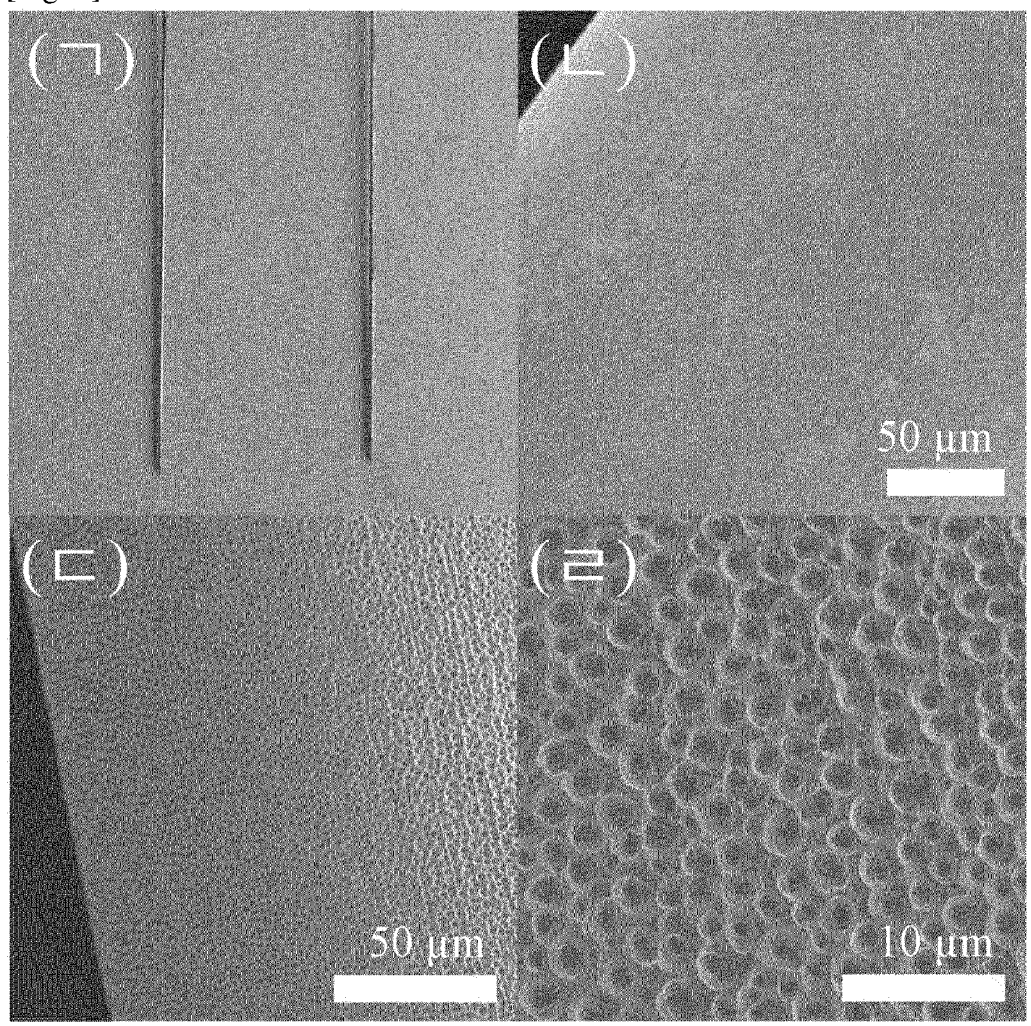
[Fig. 3]
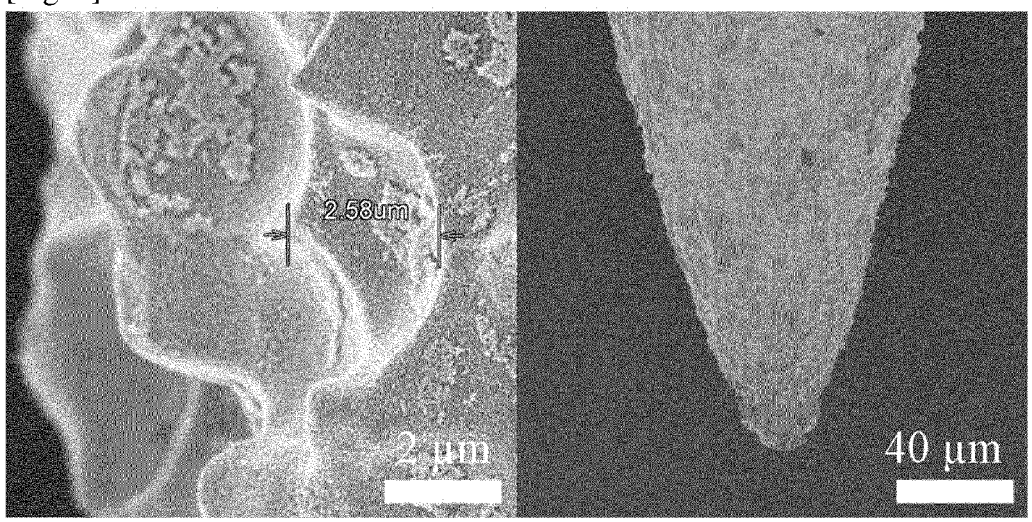

[Fig. 4]
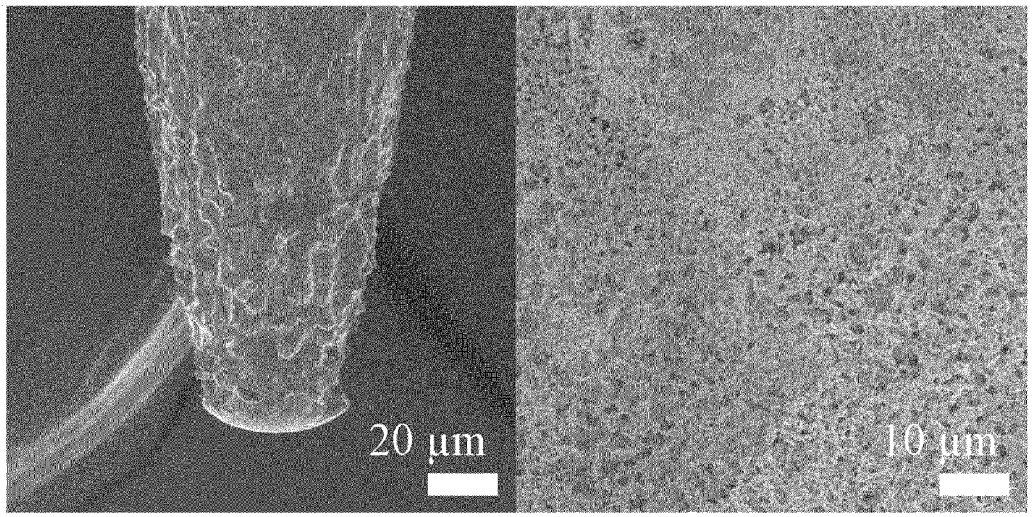
[Fig. 5]
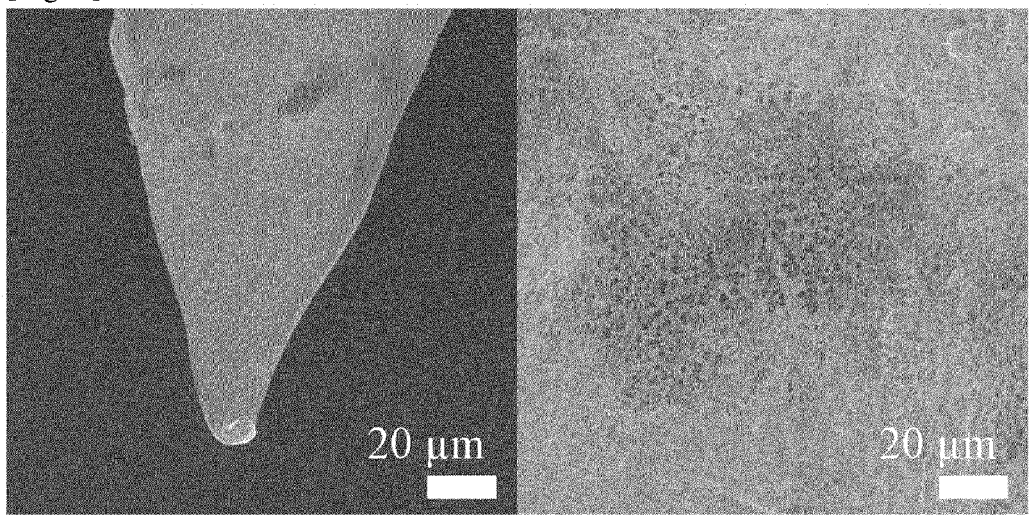
[Fig. 6]
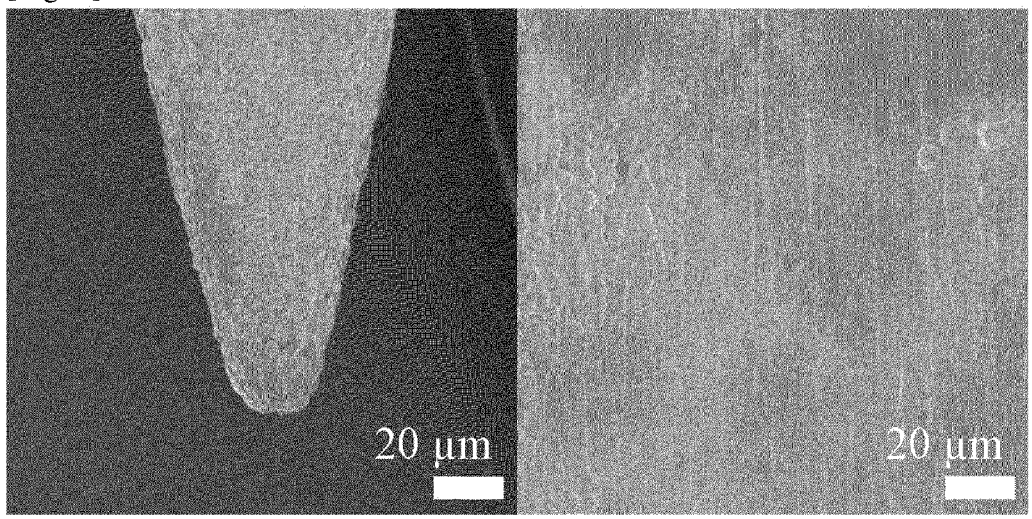

[Fig. 7]
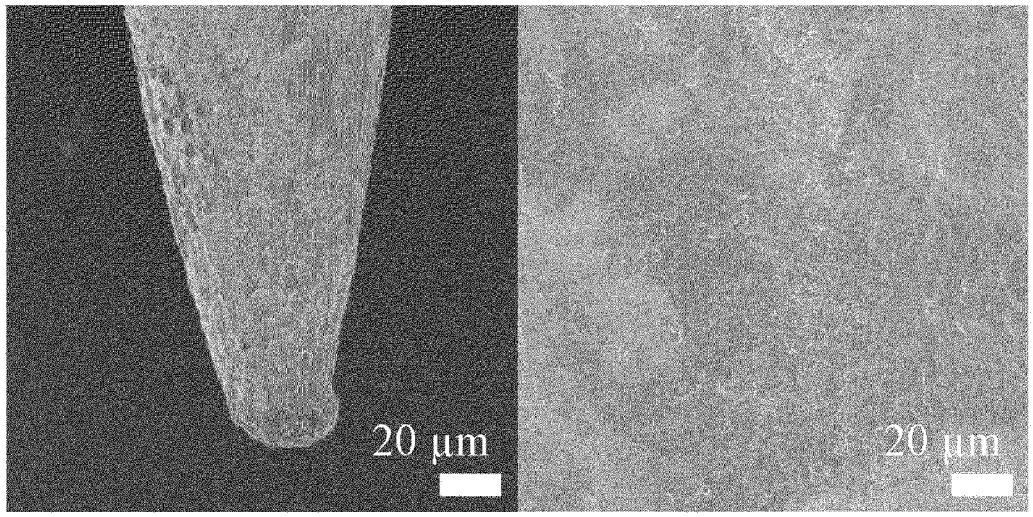
[Fig. 8]
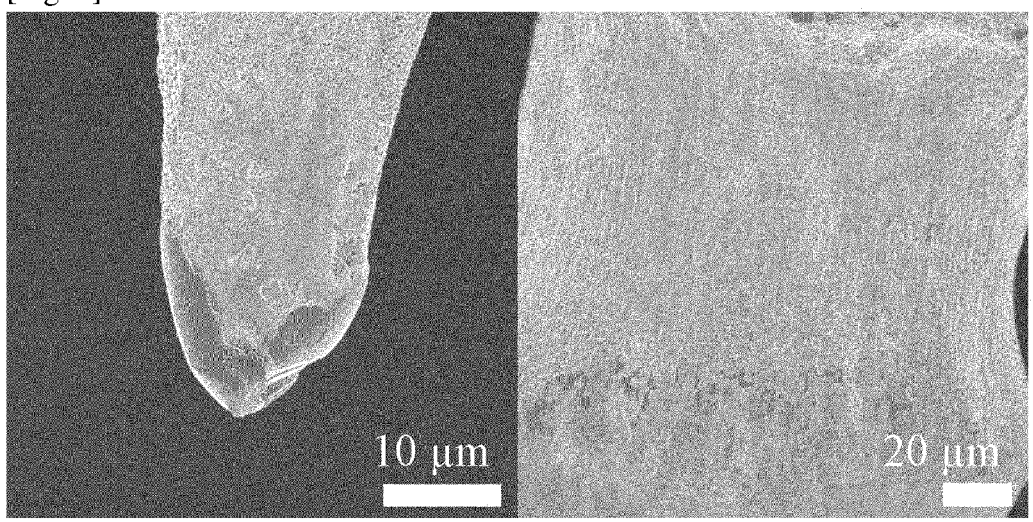
[Fig. 9]
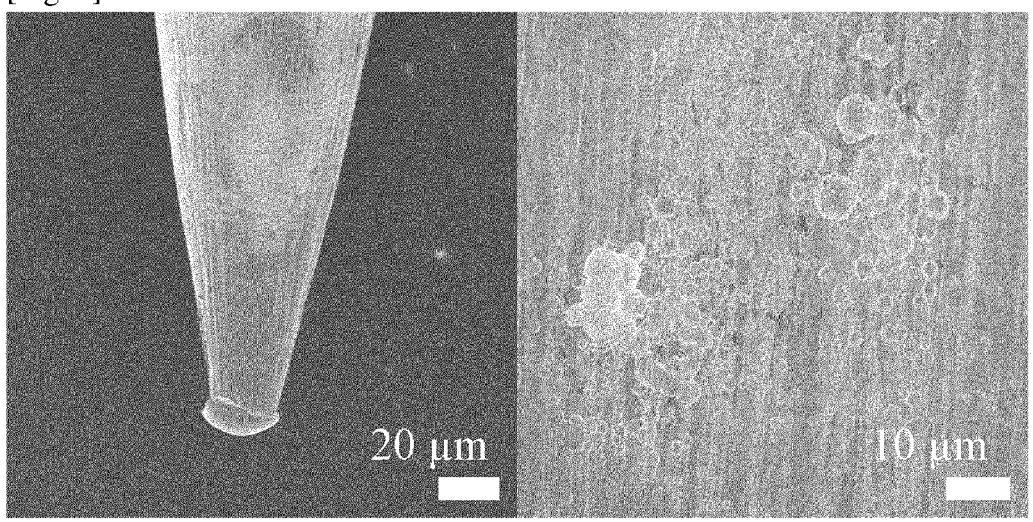

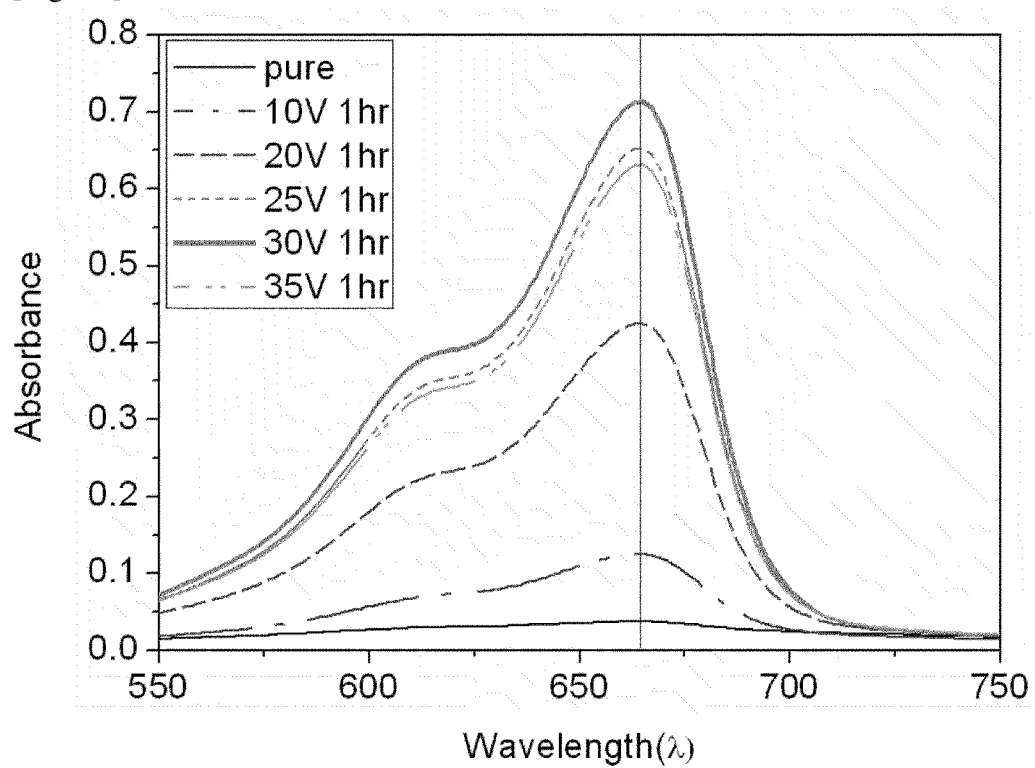
[Fig. 10]

[Fig. 11]
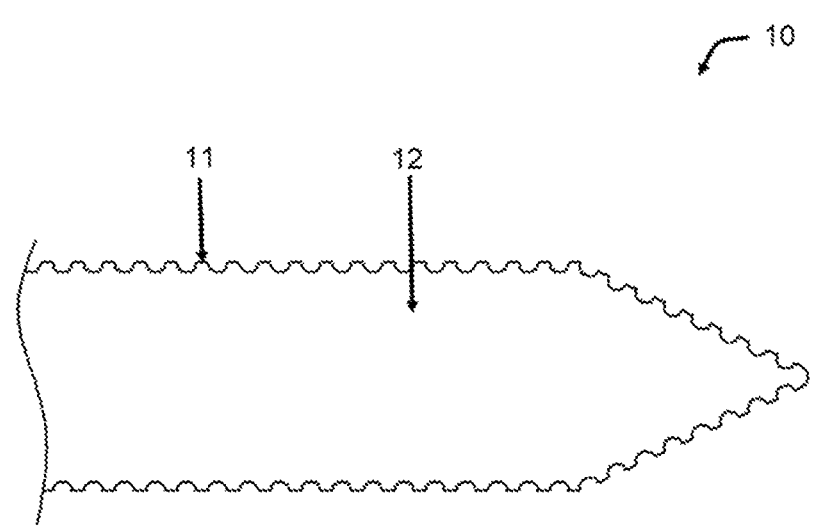

POROUS ACUPUNCTURE NEEDLE AND METHOD FOR MANUFACTURING SAME

CROSS-REFERENCE TO RELATED APPLICATIONS

This application is a national phase application under 35 U.S.C. § 371 of International Application No. PCT/KR2014/006505, filed Jul. 17, 2014, which claims priority to South Korea Patent Application No. 10-2014-0022655, filed Feb. 26, 2014. The contents of each of the above-referenced applications are incorporated into the present application by reference.

TECHNICAL FIELD

The present invention relates to an acupuncture needle having a surface on which a plurality of microscale or nanoscale holes are formed and a preparation method thereof.

BACKGROUND ART

Needles are devices manufactured to pass through skin, and typically formed of metal with proven strength and biological safety. As illustrated in FIG. 1, a conventional acupuncture needle has a needle point, a needle body and a needle handle, and is formed of materials such as stone, gold, silver, copper, iron, bone, thorns, etc. In recent years, with the development of technology, stainless steel 304 or 316L and the like is being used as a material of a needle, which is sturdy, not easily broken, resistant to corrosion and harmless to a human body.

Since pain felt by a patient upon insertion of a needle varies according to the thickness and surface condition of a commonly used injection needle, many conventional technologies have been developed in a direction of reducing the degree of pain of the patient. For example, a silicone layer is applied onto a needle surface as a method for reducing friction between the needle and human tissue upon insertion of a needle, or a needle surface is processed to be smooth to decrease surface roughness to reduce resistance generated upon insertion of a needle, thereby reducing pain felt by a patient. Furthermore, as the thickness of the needle becomes thinner, a smaller amount of pain of the patient is generated upon insertion of the needle, and thus thinner needles are increasingly being manufactured and used.

The purpose of use of an injection needle (needle for injection) is to inject a certain drug into body tissues such as blood vessels, muscles or the like through the injection needle, while a direct therapeutic effect is not expected by insertion of an injection needle itself. However, an acupuncture needle intends to achieve a therapeutic effect by inserting a needle into specific areas such as meridians, acupoints or the like without the purpose of injection of a drug. Consequently, there is a fundamental difference in the purpose of injecting a needle between them.

That is, physical stimulation of body tissues by a needle upon insertion of the needle is considered important for an acupuncture needle, unlike an injection needle. However, regardless of a therapeutic effect of a needle, an acupuncture needle is produced using a similar method as that of a typical injection needle for the purpose of reduction in pain felt by a patient upon insertion of a needle. Furthermore, pain felt by a patient can be reduced according to a state of a needle surface, but there are no experimental results showing that the therapeutic effect of the needle is the same.

Conversely, according to research on a needle and tissue (H. Langevin, 2002, Faseb), a result has been reported showing that connective tissue is wound around a needle surface by turning a needle from side to side after the needle is inserted, and stimulation thus obtained exhibits the therapeutic effect of the needle. This experiment result indicates that a binding force between a needle surface and connective tissue is important to the therapeutic effect of the needle. In other words, it means that when the binding force between them is increased by changing physical properties of a needle surface, the therapeutic effect of the needle can be improved. However, technologies for reducing roughness of a needle surface has been utilized in production of an acupuncture needle until now, which indicates that research has been conducted in a direction of decreasing the binding force between them.

Further, a technology for changing physical properties of a needle surface commonly used in production of a needle is to apply a chemical material on a needle surface. An objective of this technology is largely divided into two types in accordance with a material to be applied, and there are the case where a material such as silicone or the like is applied for the purpose of lubrication and the case where a material such as salicylic acid is applied for antibacterial and therapeutic purposes. However, needles produced by these technologies have a problem of a reduced binding force between a needle surface and connective tissue.

Moreover, a material mainly used for typical injection needles and acupuncture needles is stainless steel, and SS304 and SS0316L are the most frequently used stainless steels, both of which belong to the austenitic stainless steels. One of the methods for reducing surface roughness of these stainless steels is electropolishing, which is a technology frequently used for SS304 and SS0316L in particular. Electropolishing is a technology in which when electricity is applied to a metal to be polished in an electrolyte, an initial oxidation layer with viscosity is formed on the metal due to electrolysis to form a passivation film of the metal oxide, and thereby a relatively bent and protruded surface is more shaved to have the whole surface of the metal flattened. By applying this technology, the surface roughness of the stainless steel is adjusted.

Another technology is to process a surface using a strong laser (laser ablation), which is a method of instantaneously ablating a surface material by allowing a strong laser pulse beam incident to a metal to form a pattern. At this time, the depth of the pattern can be adjusted by controlling an output of a laser. Currently, this technology is utilized not only for a metal, but also for marking the silicon wafer for manufacturing a semiconductor. Furthermore, the most frequently used method for surface-treating an acupuncture needle is mechanical grinding, which has been developed in a direction of forming a needle point and reducing surface roughness. However, it is difficult to form a surface with a directional characteristic by this technology.

Korean Laid-Open Patent Publication No. 2008-0112759 discloses a technology of preparing an acupuncture needle where an effective area of a needle surface brought in contact with connective tissue is enlarged by physically changing the needle surface to increase a binding force between them, but there is a problem of skin damage due to roughness of a needle surface.

DISCLOSURE

Technical Problem

It is an object of the present invention to provide a new acupuncture needle which can prevent skin damage due to surface roughness of existing acupuncture needles and effectively deliver a drug to the human body through an acupuncture needle, and a method of effectively preparing the above-described acupuncture needle.

Technical Solution

In order to achieve the object, an aspect of the present invention relates to a porous acupuncture needle, including 5 to 20 holes per 100 μm² surface area (width×length, 10 μm×10 μm).

According to a preferred embodiment of the present invention, in the porous acupuncture needle of the present invention, the hole has an average diameter in a range of 0.05 to 3 μm, and has an average depth in a range of 1 to 3 μm.

According to a preferred embodiment of the present invention, in the porous acupuncture needle of the present invention, the hole is loaded with a drug.

According to a preferred embodiment of the present invention, in the porous acupuncture needle of the present invention, when a specific surface area is measured according to a method in which a specific surface area is calculated after measuring an amount of a methylene blue solution stained at a surface of an acupuncture needle, the specific surface area is 0.0100 m²/g or more, and preferably in a range of 0.0150 to 0.0350 m²/g.

According to a preferred embodiment of the present invention, the porous acupuncture needle of the present invention includes iron (Fe) at 45 to 46%, chromium (Cr) at 17 to 19%, carbon (C) at 30 to 34%, nickel (Ni) at 2 to 3% and aluminum (Al) at 1.5 to 2%.

Another aspect of the present invention relates to a method of preparing the afore-mentioned porous acupuncture needle, in which the porous acupuncture needle is prepared by forming a porous structure at a surface of the needle by performing an anodizing process.

According to a preferred embodiment of the present invention, a process of cleaning a needle may be carried out before the anodizing process, and the cleaning process may be performed by sonicating a needle before undergoing the anodizing process in acetone, sonicating the needle in ethanol, and then sonicating the needle again in purified water.

According to a preferred embodiment of the present invention, the anodizing process is performed in an electrolyte containing the needle and a carbon electrode, the needle is used as a positive electrode and the carbon electrode is used as a negative electrode, and the anodizing process is performed by applying a direct current voltage of 20 to 38V for 30 minutes to 2 hours.

According to another preferred embodiment of the present invention, in the preparation method of the present invention, the electrolyte includes one or more selected from an ethylene glycol aqueous solution and a glycerol aqueous solution.

According to still another preferred embodiment of the present invention, in the preparation method of the present invention, the electrolyte is an ethylene glycol aqueous solution including ammonium fluoride at 0.1 to 0.5 parts by weight and water at 1 to 5 parts by weight.

According to yet another preferred embodiment of the present invention, in the preparation method of the present invention, a needle before undergoing the anodizing process includes iron (Fe) at 43.5 to 45%, chromium (Cr) at 11.5 to 13%, carbon (C) at 35 to 37%, nickel (Ni) at 5 to 6.5% and aluminum (Al) at 0.5 to 1.2% when measured by an energy dispersive spectrometer (EDS).

According to yet another preferred embodiment of the present invention, in the preparation method of the present invention, a porous acupuncture needle after undergoing the anodizing process includes iron (Fe) at 45 to 46%, chromium (Cr) at 17 to 19%, carbon (C) at 30 to 34%, nickel (Ni) at 2 to 3% and aluminum (Al) at 1.5 to 2% when measured by an energy dispersive spectrometer (EDS).

Advantageous Effects

The acupuncture needle of the present invention has inwardly concave holes instead of having an outwardly protruding shape to cause no skin damage problem, since a surface area is drastically increased due to microscale or nanoscale holes uniformly formed on the needle surface, a physiological treatment effect of the needle can be increased. Furthermore, a drug can be delivered to the human body by being loaded in holes formed on the needle surface, and thus the effect due to the needle can be maximized.

DESCRIPTION OF DRAWINGS

FIG. 1 is a schematic view illustrating a preparation method as one example of a method of preparing a porous acupuncture needle of the present invention by an anodizing method.

FIG. 2 shows scanning electron microscope (SEM) images of surfaces of acupuncture needles before and after undergoing an anodizing process, where a left acupuncture needle in FIG. 2(a) is an acupuncture needle before undergoing an anodizing process and a right acupuncture needle in FIG. 2(a) is a porous acupuncture needle after undergoing an anodizing process, FIG. 2(b) is an SEM image of an acupuncture needle before undergoing an anodizing process, and FIG. 2(c) and FIG. 2(d) are SEM images of an acupuncture needle after undergoing an anodizing process.

FIGS. 3 to 9 are SEM images, respectively, of porous acupuncture needles prepared in Examples 1 to 7.

FIG. 10 shows results of absorbance measurement for measuring a specific surface of a porous acupuncture needle, which is conducted in Preparation Example 3.

FIG. 11 illustrates a porous acupuncture needle of the present invention where no layer is formed between the surface (11) and the interior (12) of the needle (10).

MODES OF THE INVENTION

The term "hole" used herein refers to a concave hole inwardly formed from a needle surface.

Hereinafter, the present invention will be described in further detail.

An acupuncture needle of the present invention relates to an acupuncture needle with a porous surface, which may be prepared by forming microscale or nanoscale holes on a needle surface by performing an anodizing process.

Further, a needle before undergoing an anodizing process may be used after undergoing through a cleaning process. Here, the cleaning process is for removing foreign matter on a needle surface and may be carried out using typical methods in the related art, and preferably, may be performed by sequentially sonicating a needle in acetone and in ethanol, and sonicating the needle again in purified water. Here, each sonication time is not particularly limited, and is preferably 5 to 20 minutes.

Moreover, any needle generally available on the market may be utilized as the needle before undergoing the anodizing process, and preferred is a needle including iron (Fe)

at 43.5 to 45%, chromium (Cr) at 11.5 to 13%, carbon (C) at 35 to 37%, nickel (Ni) at 5 to 6.5% and aluminum (Al) at 0.5 to 1.2% when measured by an energy dispersive spectrometer (EDS).

Furthermore, in regard to the anodizing process, microscale or nanoscale holes as shown in FIG. 2 may be formed on a needle surface by applying a direct current (DC) voltage of 20 to 38V, preferably 25 to 35 V, more preferably 28 to 32V for 30 minutes to 2 hours after respectively connecting a needle and a carbon electrode to a positive electrode and a negative electrode, and immersing the needle and carbon electrode in an electrolyte. When the voltage is less than 20 V, no hole may be formed on a surface of an acupuncture needle, and when the voltage is more than 38V, an acupuncture needle may be oxidized and broken. Accordingly, it is preferable to apply the voltage within the aforementioned range.

In the present invention, any electrolyte typically utilized in an anodizing process in the related art may be employed as the electrolyte used in the anodizing process, and preferred is an electrolyte including one or more selected from an ethylene glycol aqueous solution and a glycerol aqueous solution. As a specific example, an ethylene glycol aqueous solution containing ammonium fluoride ($NH_4F$) at 0.1 to 0.5 parts by weight, water at 1 to 5 parts by weight and ethylene glycol as the remaining amount may be used.

In the ethylene glycol aqueous solution, the ammonium fluoride ($NH_4F$) serves to bind to oxidized components of an acupuncture needle such that the components are dissolved in an aqueous solution and the content thereof is 0.1 to 0.5 parts by weight, and preferably 0.2 to 0.4 parts by weight. Here, when the content is less than 0.1 parts by weight, the number of holes formed on a surface of an acupuncture needle may be reduced and an average depth and size of holes may also decrease, and when the content is more than 0.5 parts by weight, formation of holes on a surface of an acupuncture needle is not achieved and a needle may be cracked. Thus, the content is preferably within the aforementioned range.

An average diameter and average depth of holes may be adjusted by controlling the above-described anodizing process conditions such as voltage intensity, an anodizing process time, a concentration of $NH_4F$, etc. Here, the average diameter and average depth of holes tend to increase when the voltage, the anodizing process time or the concentration of $NH_4F$ increases. As a preferred example, the anodizing process may be carried out under conditions of a voltage intensity of 30 V, the anodizing process time of one hour and the concentration of $NH_4F$ of 0.3 parts by weight. At this time, the depth and/or size of holes may be adjusted by increasing or decreasing each of the voltage intensity, the anodizing process time and the concentration of $NH_4F$.

An average diameter of holes formed on a needle after undergoing the aforementioned anodizing process may be 3 μm or less, preferably 0.05 to 3 μm, and more preferably 0.05 to 1 μm. Further, an average depth of the formed holes may be in the range of 1 to 3 μm, and preferably 2 to 3 μm.

A needle before undergoing an anodizing process experiences no change in the components, after undergoing an anodizing process. For example, when a needle with the aforementioned components before undergoing an anodizing process is subject to the anodizing process, the needle has the components of 45 to 46% of Fe, 17 to 19% of Cr, 30 to 34% of C, 2 to 3% of Ni and 1.5 to 2% of Al when measured by EDS, from which it can be seen that there is no large change in the components of the acupuncture needle within the error range of the measurement.

Further, a porous acupuncture needle also may be prepared by cleaning a porous needle prepared by performing an anodizing process in the aforementioned manner with purified water, and sonicating the needle in an acetone-containing solution.

As such, the porous acupuncture needle of the present invention which is prepared by an anodizing process may have 5 to 20, preferably 8 to 20, more preferably 10 to 20 concave holes per 100 $\mu m^2$ surface area (width×length, 10×10 μm). Moreover, when a specific surface area of the porous acupuncture needle of the present invention is measured according to a method in which a specific surface area is calculated after measuring an amount of a methylene blue solution stained at a surface of the acupuncture needle, the specific surface area may be 0.0100 $m^2/g$ or more, preferably 0.0150 to 0.0350 $m^2/g$, and more preferably 0.0300 to 0.0350 $m^2/g$. Due to this high specific surface area, electron delivery capabilities of the nervous system positioned at meridians are enhanced, resulting in an increase in therapeutic efficacy of acupuncture.

Furthermore, the therapeutic efficacy of acupuncture can also be increased by loading a drug in holes formed on the porous acupuncture needle of the present invention to directly deliver a drug to the human body.

Hereinafter, the present invention will be more specifically described by way of examples, but the following examples should not be construed as limiting the present invention, and are intended to be exemplary only.

EXAMPLE

Example 1

Acupuncture needles commercially available from Dongbang Medical Co., Ltd. each were sonicated at 40 kHz for 10 minutes in acetone, ethanol and purified water for cleaning. A needle at a left side of FIG. 2(a) is an acupuncture needle after cleaning.

Next, as illustrated in FIG. 1, after the cleaned acupuncture needle was connected to a positive electrode and a carbon electrode was connected to a negative electrode, the acupuncture needle and carbon electrode were put into an electrolyte, and were subjected to an anodizing process with DC 30 V for one hour to prepare a porous acupuncture needle as shown in FIG. 2(a), where the right acupuncture needle is a porous acupuncture needle after undergoing an anodizing process.

Here, 50 ml of an ethylene glycol ($C_2H_4(OH)_2$) aqueous solution containing ammonium fluoride ($NH_4F$) at 0.3 parts by weight and purified water at 2 parts by weight was used as the electrolyte in the anodizing process.

Experimental Example 1: SEM Measurement

An SEM (product name: S-4800, manufactured by Hitachi, Ltd.) image of an acupuncture needle before undergoing an anodizing process used in Example 1 is shown in FIG. 2(b), and SEM images of a surface of the porous acupuncture needle prepared in Example 1 are shown in FIG. 2(c), FIG. 2(d) and FIG. 3. It can be seen from comparison of SEM images of FIG. 2(b), FIG. 2(c) and FIG. 2(d) that an acupuncture needle before undergoing an anodizing process has a smooth surface, but a plurality of holes with a size of 3,000 nm or less are formed thereon after undergoing an anodizing process.

Further, it can be seen from FIG. 2(d) that 10 or more holes per 100 μm² surface area (width×length, 10 μm×10 μm) are formed.

Moreover, it can be seen from FIG. 3 that holes are formed to have a depth of approximately 2.58 μm.

Experimental Example 2: EDS Measurement

A change in the components of an acupuncture needle was measured by EDS measurement for acupuncture needles before and after undergoing an anodizing process, and the results are presented in the following Table 1.

Here, the EDS measurement was conducted by detecting and analyzing a certain X-ray obtained by radiating a high-energy beam of 20 keV onto a needle surface.

TABLE 1

| Compo-nents | Classification | | | |
|---|---|---|---|---|
| | Acupuncture needle before undergoing anodizing process | | Acupuncture needle after undergoing anodizing process | |
| | Atom. C (at. %) | Error (%) | Atom. C (at. %) | Error (%) |
| Fe | 44.76 | 1.76 | 45.47 | 1.28 |
| Cr | 12.19 | 0.50 | 18.29 | 0.55 |
| C | 36.29 | 2.73 | 31.75 | 2.31 |
| Ni | 5.69 | 0.34 | 2.76 | 0.18 |
| Al | 1.08 | 0.09 | 1.73 | 0.12 |

It can be seen from the results of EDS measurement in Table 1 that there is no change in the components of the acupuncture needles before and after undergoing an anodizing process, that is, there is substantially no change in the components of the acupuncture needles before and after undergoing an anodizing process considering an error range generated due to EDS characteristics.

Example 2

A porous acupuncture needle was prepared in the same manner as in Example 1 except that 35 V of a DC voltage was applied for one hour. A SEM measurement was performed in the same manner as in Experimental Example 1, and the result is presented in FIG. 4.

It can be seen from FIG. 4 that holes are well formed, but the uniformity of holes is lower than that of Example 1.

Example 3

A porous acupuncture needle was prepared in the same manner as in Example 1 except that 40 V of a DC voltage was applied for one hour. A SEM measurement was performed in the same manner as in Experimental Example 1, and the result is presented in FIG. 5. It can be seen from FIG. 5 that holes are partially formed, but are non-uniformly distributed, and there is a problem of breakage of the needle.

Example 4

A porous acupuncture needle was prepared in the same manner as in Example 1 except that 25 V of a DC voltage was applied for one hour. A SEM measurement was performed in the same manner as in Experimental Example 1, and the result is presented in FIG. 6, from which it can be seen that holes are well formed, but the uniformity of holes is lower than that of Example 1.

Example 5

A porous acupuncture needle was prepared in the same manner as in Example 1 except that 20 V of a DC voltage was applied for one hour. A SEM measurement was performed in the same manner as in Experimental Example 1, and the result is presented in FIG. 7, from which it can be seen that holes are well formed, but the uniformity of holes is lower than that of Example 1.

Example 6

A porous acupuncture needle was prepared in the same manner as in Example 1 except that 50 V of a DC voltage was applied for one hour. A SEM measurement was performed in the same manner as in Experimental Example 1, and the result is presented in FIG. 8, from which it can be seen that there is a problem of breakage of the acupuncture needle, and although holes are partially formed, most of the surface of the acupuncture needle is formed like being melted down.

Example 7

A porous acupuncture needle was prepared in the same manner as in Example 1 except that 10 V of a DC voltage was applied for one hour. A SEM measurement was performed in the same manner as in Experimental Example 1, and the result is presented in FIG. 9. It can be seen from FIG. 9 that almost no holes are formed.

Experimental Example 3: Specific Surface Area Measurement Test

A specific surface area test was performed on porous acupuncture needles prepared in Examples 1 to 7, and the results are presented in the following Table 2 and FIG. 10. Further, the specific surface area test was conducted as follows: an acupuncture needle was immersed in a methylene blue solution, was removed to be loaded into a beaker with distilled water and shaken such that all the methylene blue solution loaded on the acupuncture needle was dissolved in distilled water. Next, the absorbance of distilled water having the methylene blue solution dissolved therein was measured to determine an amount of methylene blue loaded on the porous acupuncture needle, by which a measurement was performed according to a method in which a specific surface area was calculated after measuring an amount of a methylene blue solution stained at a surface of an acupuncture needle. Here, as for the method of calculating a specific surface area, the absorbance of a methylene blue solution loaded on acupuncture needles before and after undergoing an anodizing process was measured according to the following Equation 1 to calculate a concentration of methylene blue, and then the value was substituted into the following Proportional Expression 1 to measure a specific surface area.

$$\text{Concentration (M)} = 1.667e^{-5} \text{ (M/Abs)} \times \text{Absorption (Abs)}$$

In Equation 1, $1.667\,e^{-5}$ (M/Abs) is a conversion factor obtained by an absorbance test for a methylene blue solution with a known concentration.

$$\text{Concentration 1:} 0.0017 \text{ (m}^2\text{/g)} = \text{Concentration 2:specific surface area of acupuncture needle after undergoing anodizing process} \quad \text{[Proportional Expression 1]}$$

In Proportional Expression 1, Concentration 1 is a concentration of methylene blue loaded on an acupuncture needle before undergoing an anodizing process, and Concentration 2 is a concentration of a concentration of methylene blue loaded on an acupuncture needle after undergoing an anodizing process. Further, the specific surface area before undergoing an anodizing process is 0.0017 (m$^2$/g), which is calculated by a thickness, length and weight of the needle.

TABLE 2

| Classi-fication | Voltage intensity (V) | Specific surface area (m$^2$/g) | Number of holes per 100 μm$^2$ surface area | Notes |
|---|---|---|---|---|
| Example 1 | 30 | 0.0328 | 10 to 15 | Optimum conditions |
| Example 2 | 35 | 0.0291 | 5 to 8 | Hole uniformity is slightly lower than that of Example 1 |
| Example 3 | 40 | Not measured | Not measured | Acupuncture needle is broken |
| Example 4 | 25 | 0.0301 | 5 to 6 | Hole uniformity is slightly lower than that of Example 1 |
| Example 5 | 20 | 0.0196 | 2 to 3 | Hole uniformity is slightly lower than that of Example 1 |
| Example 6 | 50 | Not measured | Not measured | Acupuncture needle is broken |
| Example 7 | 10 | 0.0058 | 0 | Almost no holes |

It can be seen from Table 2 that a specific surface area was 0.0100 m$^2$/g or more in the case of Examples 1, 2, 4 and 5 where an anodizing process was carried out a DC voltage intensity of 20 to 38V.

However, in the case of Examples 3 and 6 with DC intensities voltages of 40 V and 50 V, acupuncture needles were broken and a hole was not substantially formed, and thus it was impossible to measure a specific surface area.

Furthermore, in the case of Example 7 with a DC voltage intensity of 10 V, there was a lack of formed holes, resulting in a low specific surface area of 0.0100 m$^2$/g.

It can be seen from FIG. 10 that Example 1 where an anodizing process was performed with a voltage intensity of 30 V showed the highest absorbance, and porous acupuncture needles in Examples 2 and 4 where an anodizing process was performed with voltage intensities of 35 V and 25 V also had high absorbance. Further, the absorbance of Example 5 with a voltage intensity of 20 V was lower than those of Examples 1, 2 and 4, but was significantly higher than that of Example 7 with a voltage intensity of 10 V.

Preparation Example 1: Preparation of Porous Acupuncture Needle Loaded with Drug A drug was loaded into holes of a porous acupuncture needle by immersing the porous acupuncture needle prepared in Example 1 in a methylene blue solution.

Further, according to the result of measuring a weight of the porous acupuncture needle loaded with a dye, the weight of the acupuncture needle was 0.1517 g before loading a dye, and was 0.01520 g after loading a dye, that is, the weight of the porous acupuncture needle increased by about 0.2%, from which it can be determined that a drug was effectively loaded into the holes.

It can be seen from the examples and experimental examples that the porous acupuncture needle of the present invention has a surface on which holes are well formed to have a high specific surface area, and a drug is also well loaded into the holes formed on the surface area. As illustrated in FIG. 11, no layer is formed between the surface (11) and the interior (12) of the needle (10). It is expected that a huge increase in acupuncture therapeutic effect can be achieved by using the porous acupuncture needle of the present invention.

The invention claimed is:

1. A porous acupuncture needle having an interior and a surface both comprising iron (Fe) at 45% to 46%, chromium (Cr) at 17% to 19%, carbon (C) at 30% to 34%, nickel (Ni) at 2% to 3%, and aluminum (Al) at 1.5% to 2%, when measure by an energy dispersive spectrometer (EDS), wherein no layer is formed between the surface and the interior, wherein the surface forms 5 to 20 holes per 100 μm$^2$ of the surface area, and wherein the surface area of the porous acupuncture needle is 0.0150 to 0.0350 m2/g as calculated by measuring methylene blue solution staining of the surface.

2. The porous acupuncture needle of claim 1, wherein each hole has an average diameter in a range of 0.05 to 3 μm.

3. The porous acupuncture needle of claim 1, wherein each hole has an average depth in a range of 1 to 3 μm.

4. The porous acupuncture needle of claim 1, wherein each hole is loaded with a drug.

5. A method of preparing a porous acupuncture needle having an interior and a surface, the method comprising forming a porous structure on the needle surface by performing an anodizing process in an electrolyte containing the needle and a carbon electrode, the needle is used as a positive electrode and the carbon electrode is used as a negative electrode, and the anodizing process is performed by applying a direct current voltage of 20 to 38V for 30 minutes to 2 hours, wherein the surface and interior both comprise iron (Fe) at 45% to 46%, chromium (Cr) at 17% to 19%, carbon (C) at 30% to 34%, nickel (Ni) at 2% to 3%, and aluminum (Al) at 1.5% to 2%, when measure by an energy dispersive spectrometer (EDS), wherein no layer is formed between the surface and the interior, and wherein the surface forms 5 to 20 holes per 100 μm$^2$ of the surface area.

6. The method of claim 5, wherein the electrolyte includes one or more selected from an ethylene glycol aqueous solution and a glycerol aqueous solution.

7. The method of claim 5, wherein the electrolyte is an ethylene glycol aqueous solution including ammonium fluoride at 0.1 to 0.5 parts by weight and water at 1 to 5 parts by weight.

* * * * *